United States Patent [19]

Hawkins, deceased

[11] 4,085,007
[45] Apr. 18, 1978

[54] METHOD AND APPARATUS FOR CONDUCTING FERMENTATION

[75] Inventor: Harold M. Hawkins, deceased, late of Bartlesville, Okla., by Marjorie Wood Hawkins, executrix

[73] Assignee: Phillips Petroleum Company, Bartlesville, Okla.

[21] Appl. No.: 677,209

[22] Filed: Apr. 15, 1976

Related U.S. Application Data

[62] Division of Ser. No. 545,547, Jan. 30, 1975, Pat. No. 3,985,622.

[51] Int. Cl.² ............................................. C12B 1/14
[52] U.S. Cl. ..................................................... 195/109
[58] Field of Search ................................. 195/109, 142

[56] References Cited

U.S. PATENT DOCUMENTS

| | | | |
|---|---|---|---|
| 3,114,677 | 12/1963 | Stich | 195/142 |
| 3,642,577 | 2/1972 | Gorring | 195/142 |
| 3,769,176 | 10/1973 | Hise et al. | 195/109 |
| 3,793,152 | 2/1974 | Sassa | 195/109 |
| 3,847,748 | 11/1974 | Gibson et al. | 195/109 |

*Primary Examiner*—Alvin E. Tanenholtz

[57] ABSTRACT

An apparatus for the aerobic fermentation of microorganisms, with the apparatus including a vessel having an elongate tubular member connected thereto and forming a fermentation zone. A pump is provided to effect flow of fermentation medium from the vessel through the tubular member for fermentation therein and back to said vessel. During flow of fermentation medium through the tubular member, oxygen is introduced into same to carry out the fermentation process. A heat exchanger cooperates with the tubular member to remove heat from the fermentation medium which is produced by the fermentation process. A second vessel can be connected to the vessel for receipt of foam containing product therein to separate the foam into a liquid phase and a gas phase.

8 Claims, 2 Drawing Figures

METHOD AND APPARATUS FOR CONDUCTING FERMENTATION

This is a division of application Ser. No. 545,547, now U.S. Pat. No. 3,985,622 filed Jan. 30, 1975.

In fermentation processes such as those involving the aerobic fermentation of microorganisms for the production of single cell protein, vessels are normally employed. The vessel size is dependent on the production rate and vary from laboratory experimental size up to multimillion liter sizes. Typically, the entire fermentation process is carried out in the vessel, the process including aerobic fermentation, feeding of nutrient and carbon source, injection of oxygen, flow of fermentation medium and separation of gas and liquid phases which involves the use of structure which is generally installed within the vessel. Fermentation processes are exothermic and release large quantities of heat which must be removed by heat exchangers which are normally mounted in the interior of the vessel or can be external of the vessel. Because of the large amount of heat produced, the heat exchangers must have large surface area to remove the heat at a rate sufficient to maintain proper growth temperature within the vessel. This complicates the design and construction of fermentation vessels and increases the physical size thereof. Because of the amount of components that must be within the vessel, cleaning and sterilizing is difficult and maintenance of the vessel and components thereof is complicated.

It is therefore a principal object of the present invention to simplify the construction of the fermentation apparatus. Other objects and advantages of the present invention are: to provide a fermentation apparatus which permits the use of a vessel having a reduced size and simplified construction; to provide such an apparatus which permits the use of large surface area for heat exchange to adequately remove heat produced by the fermentation process; to provide such an apparatus which can have the majority of the components thereof constructed from commercially available components; to provide such an apparatus which has improved operating capabilities; to provide such an apparatus which can be relatively horizontally disposed so as to reduce hydrostatic head normally found in vessel type fermentation apparatus; and to provide such an apparatus which is simple to construct, easy to maintain and well adapted for its intended use.

Other objects and advantages of the present invention will become apparent from the following detailed description taken in connection with the accompanying drawings wherein are set forth by way of illustration and example certain embodiments of this invention.

Figure 1:
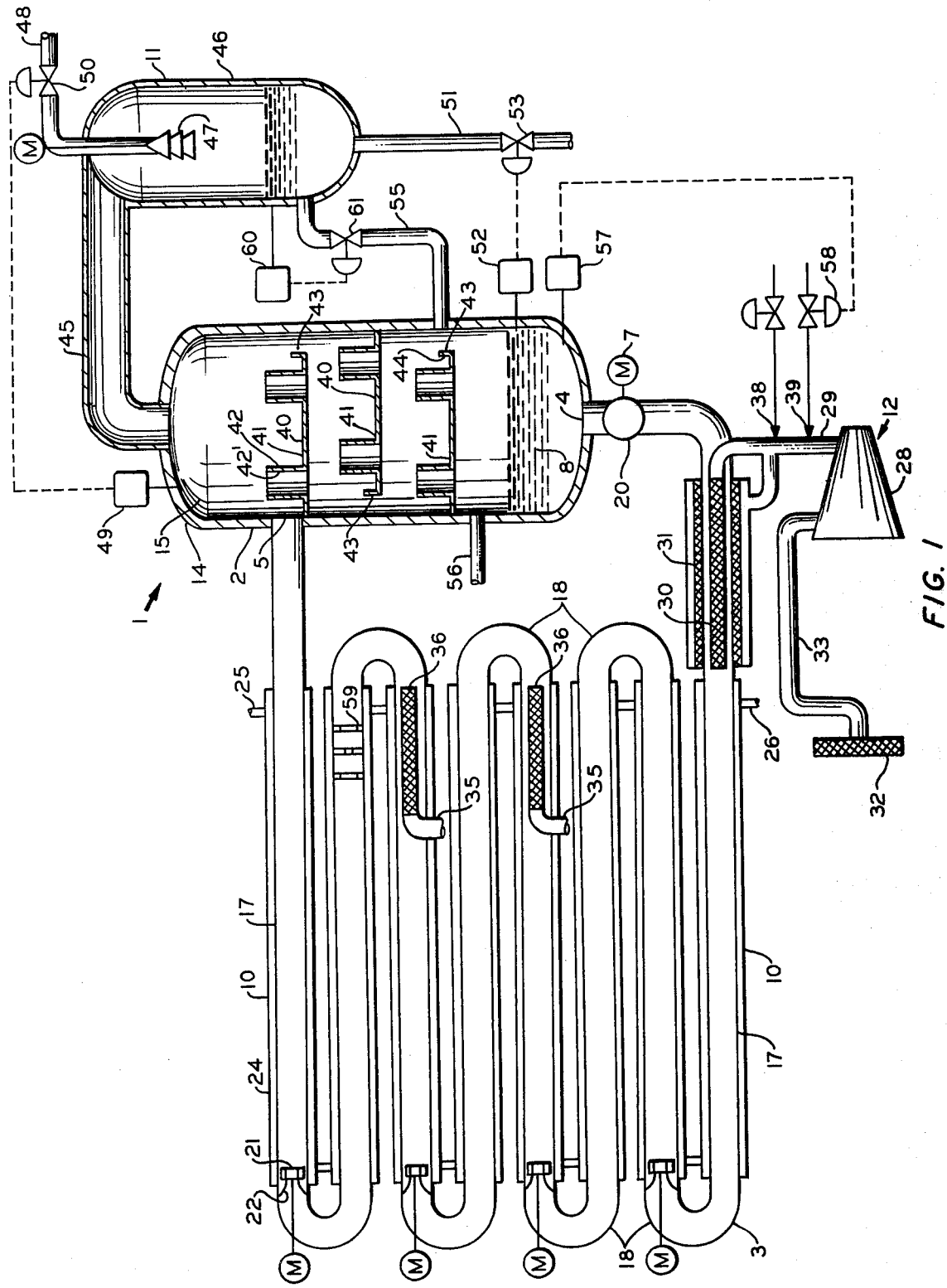
FIG. 1 is a diagramatic view of a fermentation apparatus.

As required, detailed embodiments of the present invention are disclosed herein, however, it is to be understood that the disclosed embodiments are merely exemplary of the invention which may be embodied in various forms. Therefore, specific structural and functional details disclosed herein are not to be interpreted as limiting but merely as a basis for the claims and as a representative basis for teaching one skilled in the art to variously employ the present invention in virtually any appropriate detailed structure.

Referring more in detail to the drawings:

The reference number 1 designates, generally, a fermentation apparatus which includes a vessel 2, forming a separation zone, having an elongate tubular member 3, forming a reaction zone, with an inlet 4 and an outlet 5 communicating with the interior of the vessel 2. Pump means 7 are provided to help induce flow of fluid fermentation medium 8 through the tubular member 3 from the inlet 4 to the outlet 5. Heat exchange means 10 cooperates with the tubular member 3 for removing heat therefrom which is produced by the fermentation. Separator means 11, if desired, can be provided to separate a portion of the fluid medium into a gas phase and a liquid phase. Injection means 12 is connected to the tubular member and are operable for injecting an oxygen-containing gas into the fluid medium as same flows through the tubular member 3.

The vessel 2 can be of any suitable type and, as shown, is comprised of a shell portion 14 defining a hollow interior 15. Preferably, the shell is of a rigid material such as stainless steel for sanitation and corrosion resistance. The inlet 4 is preferably connected to the vessel 2 adjacent the lower disposed end thereof with the tubular member 3 extending laterally from the vessel 2 with a major portion of the tubular member preferably being horizontally disposed. As shown, the tubular member 3 is comprised of straight portions 17 connected in series by return bends 18 with the number of straight portions 17 being dependent on the reaction zone volume required for the fermentation process. The outlet 5 is connected to the vessel 2 and communicates with the interior thereof at a position preferably above the inlet 4 for a purpose later described. Although only one tubular member 3 is shown, it is to be understood that any number of same can be connected to the vessel 2 as is required by the desired operating capacity of the fermenting apparatus 1. Preferably, the tubular member 3 is made from stainless steel pipe sections which are of generally standard construction and dimension.

The pump means 7 can and, as shown, includes a motor driven pump 20 which is positioned adjacent the inlet 4 for pumping fluid medium from the vessel 2 into the tubular member 3 for circulation therethrough. Any suitable pump can be employed and is preferably a non-cavitating type. The pump means 7 can also include, if desired, pumps 21 which cooperate with the tubular member 3 and have portions thereof suitably mounted in the tubular member 3. The pumps 21 can be a turbine type or a serrated propeller type preferably which are capable of high shear pumping action for the purpose of mixing gas and liquid phases into foam. The pumps 21 are preferably positioned between the inlet 4 and outlet 5 of the tubular member to supplement the pumping or can be used in place of the pump 20 and to help maintain the fluid medium in a uniformly mixed condition. If a turbine type pump 21 is used, it can be mounted adjacent a return bend 18 wherein a nozzle or reduced diametral portion 22 can be positioned upstream of the pump 21 to direct the fluid medium flowing through the tubular member into the eye of the turbine for improved pumping.

The heat exchange means 10 cooperate with the tubular member 3 to remove heat generated by the fermentation process taking place in the tubular member 3. Any suitable heat exchange means can be provided and as shown same includes a jacket 24 which surrounds the straight pipe portions 17 forming an annular flow path therebetween for coolant to flow through. The heat exchanger around one straight pipe portion 17 can be connected in series or parallel with the remainder of the heat exchangers as by conduits between inlets 25 and outlets 26. Further, baffles (not shown) can be provided in the annular space between the jacket and the pipe portions 17 to define a suitable flow path for coolant flowing through the respective heat exchanger.

The injection means 12 can be of any suitable type which is operable to inject oxygen in some form into the liquid medium flowing through the tubular member 3. It is to be understood that the terms "oxygen" or "oxygen-containing gas" can include any suitable form of oxygen, either alone, or in combination with other substances such as air or oxygen enriched air. As shown, the injection means includes a compressor 28 which is connected to the tubular member 3 by a conduit 29 which extends into the interior of the tubular member 3. As shown, a sparging device such as a porous member 30 is suitably mounted in the tubular member 3 and is connected to the conduit 29 for the dispersion of oxygen into the fluid medium. Also, a second porous member 31 can be connected to the conduit 29 forming a porous wall opening into the tubular member 3 to allow additional injection of oxygen into the fluid medium. Preferably, the oxygen is injected in the form of air or oxygen-enriched air and is taken from the atmosphere and filtered and sterilized as required through a purification apparatus 32 which is connected to the compressor 28 by a conduit 33. It is to be noted that depending upon oxygen demand and the length of the tubular member 3, oxygen may be injected into the tubular member 3 at a plurality of positions along the length thereof between the inlet 4 and outlet 5 as by having a conduit 35 connecting a porous member 36 similar to the porous member 30 to the compressor 28. Preferably, the oxygen is dispersed in small bubbles so as to have a large surface area contact with a liquid phase by the sparging and also by the action of the pumps 21. The oxygen-to-liquid ratio is maintained at a value to maintain a foam condition and adequate for microbial growth.

Oxygen for enriching the air can be injected into the conduit 29 through a conduit 38 by any suitable means (not shown). Also, in the fermentation of microorganisms for the production of single cell protein certain nutrients are required which can also be injected into the conduit 29 through a conduit 39 by any suitable means (not shown). Such nutrients can include compounds such as ammonia and related compounds.

In the form of fermenting apparatus shown, the vessel 2 can be provided with one or more tray members 41 which preferably are secured to the shell 14 and positioned in the interior of the vessel 2 with same preferably being positioned at different heights therein. The trays 41 can be of any suitable structure preferably having an upwardly facing substantially flat surface 40. Means are provided to define openings or chimneys through the trays 41 to provide a passageway for the upward flow of foam and gas as later described. As shown, these means include duct members 42 secured to the respective trays 41 and define openings 42' therethrough with the members 42 preventing flow of heavier fluid medium downwardly through the openings formed thereby. As shown, downcomers 43 are formed for each of the trays 41 to provide a passageway through which the more dense fluid medium flows downwardly when same exceeds the level of a dam 44 which defines one edge of the respective downcomer 43. As shown, the trays are positioned such that the downcomer of one tray is positioned above the side of the next lower tray, remote from its respective downcomer whereby the fluid medium flowing over the trays flows from one edge across the tray to its respective downcomer.

Preferably, the fermenting apparatus 1 is provided with separator means 11 which is operable to separate foam produced by the fermentation process into a liquid phase and a gas phase. However, it is to be understood that chemical defoaming can be used instead of or in conjunction with the illustrated mechanical foam separator. As shown, a conduit 45 is connected to the upper portion of the vessel 2 and forms a flow path to a second vessel 46. A mechanical foam breaking device 47, of any suitable type, is provided in the vessel 46 which breaks the foam into a gas phase, which escapes through an exhaust conduit 48 or any other suitable gas vent, and a liquid phase which is collected in the lower portion of the vessel 46. It is to be noted that a pressure control apparatus 49 can be provided to sense the pressure in the vessel 2 and manipulates a valve 50 located in the exhaust conduit to maintain a desired pressure within the vessel 2 so that the fermentation apparatus 1 can be operated at a desired controlled pressure at or above atmospheric. Any suitable pressure controller and valve can be employed. A liquid discharge conduit 51 is connected to the vessel 46 adjacent the lower disposed portion thereof and is adapted for the discharge of product-containing liquid from the vessel 46. Preferably a suitable level controller 52 is operably connected to the vessel 2 to sense the level of liquid medium therein so as to manipulate valve 53 for operation thereof in response to level changes to control the discharge of liquid from the vessel 46 thereby controlling the level of liquid in the vessel 2. This can also be accomplished by having a conduit 55 form a flow path between the vessel 46 and vessel 2, preferably with a siphon trap (not shown) therein so that excess separated liquid in the vessel 46 is returned to the vessel 2 to maintain constant inventory therein.

The present invention is more fully understood by a description of the operation thereof. A nutrient-substrate solution, preferably an aqueous solution, is introduced into the vessel 2 through an inlet 56 with the nutrient typically including a carbonaceous material such as methanol and other substances necessary for the growth of a microorganism within the vessel 2. A suitable microorganism inoculum is introduced into the vessel 2 for growth therein. Although it is difficult to define the difference between foam, broth and liquid in a process of this type, the same vary by the amount of gas dispersed in a liquid phase with foam being the highest gas content, broth being the next higher gas content and liquid being the lower gas content. Foam, broth and liquid were referred to above as fluid medium. Liquid settles in the bottom of the vessel 2 and is continually removed therefrom and is pumped into the reaction zone or tubular member 3 by the pump means 7. The majority of fermentation and microbial growth are carried out in the reaction zone. Oxygen, preferably in the form of air or oxygen-enriched air, is introduced into the liquid by the injection means 12 to provide the oxygen necessary for the growth of the microorganism. The heat exchange means extend downstream of the points of oxygen introduction for removal of heat as same is produced by the microbial growth which is enhanced by the oxygen. As described above, a source of nitrogen as a nutrient can also be injected by the injection means 12 and in a preferred embodiment the source of nitrogen is a base such as ammonia which can also be used to control the pH of the fermentation process liquid. The measured pH value is controlled by a suitable pH controller 57 which is operably connected to the ammonia feed valve 58 which controls the rate at which ammonia is injected into the broth in the tubular medium. Most of the fermentation is effected within the tubular member 3 between the inlet 4 and the outlet 5 as the broth flows therethrough. Fermentation processes are generally exothermic wherein the heat released during the fermentation process must be removed by the heat exchanger 10 to maintain the process at a temperature which is suitable to induce good growth characteristics of the microorganism. As described above, oxygen can be injected at a plurality of points along the length of the tubular member to insure high oxygen concentration in the fluid medium or ferment as same flows through the tubular member. This is necessary because the microorganisms must have oxygen to grow and can deplete the dissolved oxygen in the fluid medium at high rates.

It is to be noted that a uniform broth mixture is desirable and therefore suitable static mixing devices 59 such as mixing orifice assemblies can be positioned in the tubular member 3 to help produce a uniform mixture. The pumps 21 also help induce flow of broth through the tubular member and effect some mixing thereof. The fermentation reaction takes place principally within the tubular member after which the broth is discharged back into the vessel 2 at the outlet 5. As described above, a plurality of trays 41 can be provided in the vessel 2 for increasing the surface area of the broth to improve the release of dispersed gas from the broth which helps to form the foam which collects in the upper portion of the vessel 2 and is discharged through the conduit 45 into the separator means 11. By use of a horizontally disposed reactor, i.e., the tubular member 3, the hydrostatic head can be reduced in the vessel 2 and thereby decrease the density gradient of the broth therein. The foam is a preferred product from the vessel 2 as same normally contains a higher concentration or protein cells which is a desired end product of the fermentation process. It is to be noted that product discharge can be provided such as at the lower portion of the vessel 2 or any other suitable position for removal of product other than at the upper portion of the vessel or in addition thereto. The foam is separated in the separator means 11 into a gas phase and a liquid phase with the gas phase escaping through the exhaust conduit 48 and the liquid collecting in the bottom of the vessel 46. The liquid phase can be discharged through the discharge 51 to other equipment (not shown) for further processing to separate the cell product from the liquid.

As illustrated, the conduit 55 can be connected between the vessel 46 and the vessel 2 wherein a certain amount of the liquid collected in the bottom portion of the vessel 46 can be returned to the vessel 2 for further fermentation. A controller 60 can be operably connected to a remote control valve 61 which is connected to the conduit 55 to control the rate of liquid discharge through the conduit 5 into the vessel 2. The controller senses liquid level in the vessel 46 for control of the liquid level in response to changes thereof.

The trays 41 can be of any suitable construction having openings 42' therethrough defined by the members 42 which in effect form chimneys for the escape of gas and/or foam upwardly. The broth flows over the trays 41 to a respective downcomer 43 for discharge onto the next lower tray 41 and so on down the remainder of the trays 41 in the vessel 2 to increase the surface area of foam for escape of gas therefrom and/or increase the dwell time of the fluid medium within the vessel 2 to allow the escape of dispersed gases from the fluid medium. Finally, the broth is discharged from the trays 41 and collects in the lower portion of the vessel 2 as a liquid which is then recirculated through the tubular member 3 for further fermentation.

It is to be noted that automatic control means in addition to those shown such as computer control equipment can be provided for the fermentation apparatus to monitor various parameters and control the process conducted within the apparatus.

Figure 2:
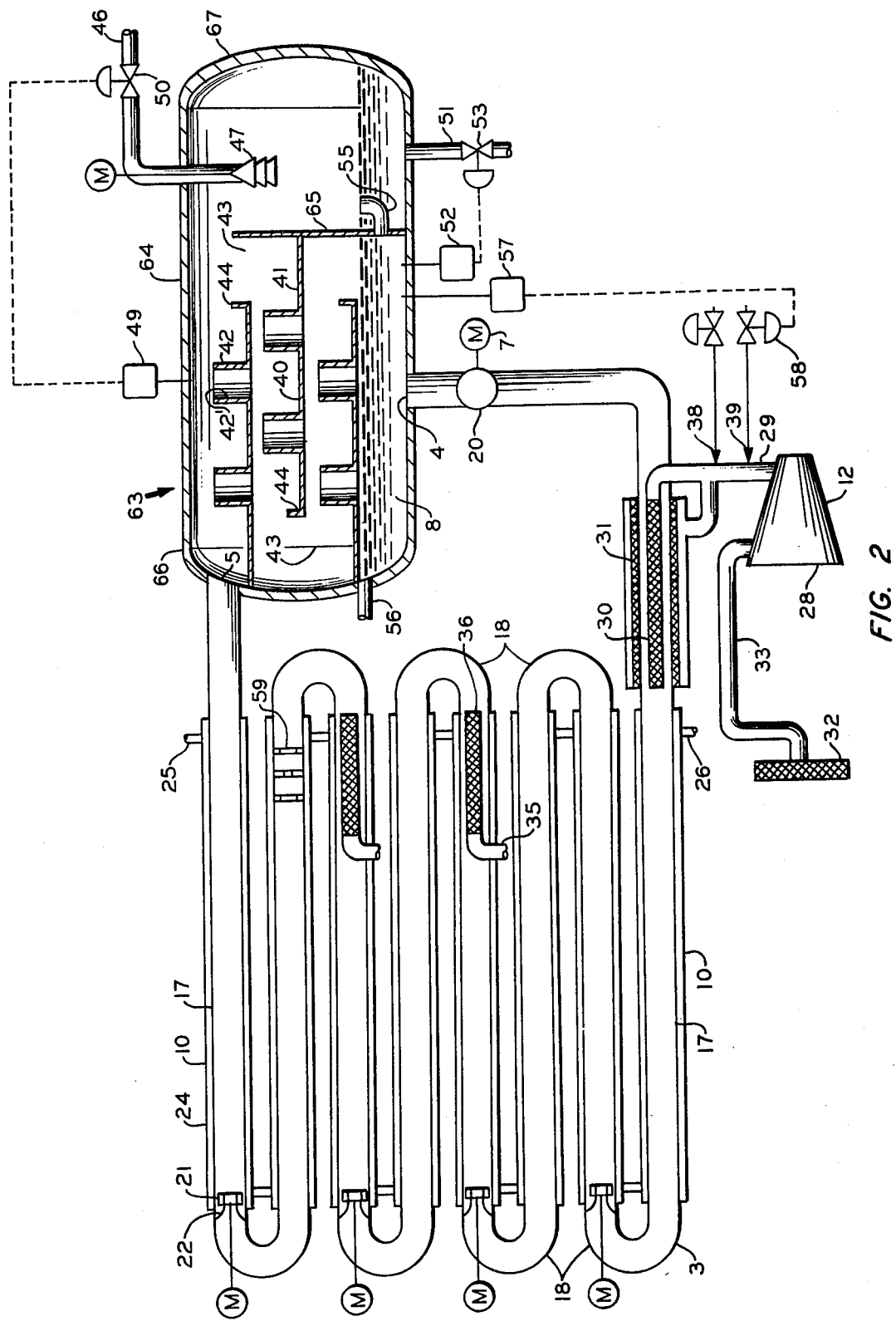
FIG. 2 is a diagrammatic view of a modified form of fermentation apparatus.

FIG. 2 shows a modified form of the present invention wherein like numbers designate like or similar parts or structure. The reference numeral 63 designates the modified fermentation apparatus wherein the major difference between the apparatus 63 is in the configuration of the vessel 2 and the vessel 46. As shown in the modified form, the fermentation apparatus 63 has a single vessel 64 with a overflow weir 65 separating two vessel portions 66 and 67 with the vessel portions 66 being the equivalent to the vessel 2 described above and the vessel portion 67 being the equivalent to the vessel 46 described above. Trays 41 are mounted in the vessel portion 66 for the production of foam and separation of gas from the broth. A foam breaking device 47 is mounted in the vessel portion 67 for separating the foam passing over the overflow weir 65 into a gas phase and a liquid phase.

Operation of the fermentation apparatus 63 is similar to operation of the fermentation apparatus 1.

The following is an example of a typical aqueous fermentation process carried out in the apparatus as described above with same being calculated on the basis of the use of bacteria in the aerobic fermentation process using methanol as the carbon and energy source. Typical operating parameters are as follows:

Cell yield — 0.39 lb/lb methanol feed;
Oxygen required — 3.0 lb $O_2$/lb cells produced;
Cell concentration — 3.0 weight percent in fermenter broth, 6.0 weight percent in liquid from foam separator;
Reaction residence time — 3 hours;
Heat of fermentation — 18,000 BTU/lb of cells;
Total flow velocity of medium in tubular member — 16 ft/sec;
Liquid/gas ratio in tubular member — approximately 1 vol/vol;
Tubular member input pressure — 45 psia;
Foam separator pressure — approximately 42 psia;
Fermentation temperature — 40° C (104° F).

For a fermenting apparatus having an approximately 10,000 gal. capacity, the following conditions would be typical as based upon the above parameters:

Cell production rate — approximately 417 lb/hr;
Tubular member — 16–40 ft. sections of 18 in. pipe with return bends connecting the straight sections;
Heat removal — jacket each section with 20 in. pipe and supply cooling water at approximately 86° F in and 91° F out with total cooling water being supplied at 3,000 GPM. Four sections of heat exchangers are connected in series (thereby producing four parallel sets) to obtain the approximate 6 ft/sec cooling water velocity in the annulus or provide baffles in the annulus to lengthen flow path of cooling water and connect all sections in parallel.

Gas dispersion — disperse approximately 14.1 cfs of air input (at 45 psia 104° F or 2350 cfm at 14.7 psia and 60° F) in the tubular member;

Foam separator — (vessel 2). The vessel would be approximately a 7 ft. diameter by 10 ft. in height vessel having three trays with approximately seven 1-ft. diameter openings therethrough and having an overflow weir preferably less than or equal to approximately 1 ft. in height;

Gas separator — (vessel 46). The vessel would be approximately 4 ft. in diameter by 7 ft. in height;

Fluid medium circulation — approximately 6350 gpm;

Pressure drop through each length of tubular member — approximately 1 psi, based on the use of a pump 21 i.e. the use of seven pumps 21.

Cooling water — flow rate 3000 gpm — 5° F rise from coolant inlet to outlet;

| Power required | pumps or impellers approximately | 150 hp total |
|---|---|---|
| | foam breaker | 40 hp |
| | air compressor | 230 hp |
| | | 420 hp |

The above values would be for a typical fermentation apparatus as disclosed but it is to be understood that the values will vary depending upon the type of microorganism used, fluid medium used and the like.

It is to be understood that while I have illustrated and described certain forms of my invention, it is not to be limited to the specific form or arrangement of parts herein described and shown.

What is claimed and desired to be secured by Letters Patent is:

1. A method for effecting microbial growth by a fermentation process comprising:
    (a) introducing fermentation medium into a reaction zone defined by a tubular member consisting of a plurality of generally horizontally disposed tubular portions connected in flow communication by at least one interconnecting member and each said tubular portion forming a substantially horizontal flow path portion of a flow path where a major portion of the reaction zone is disposed generally horizontally;
    (b) flowing said medium through said reaction zone from an inlet to an outlet during which a majority of the fermentation is conducted;
    (c) injecting an oxygen-containing gas into said medium when same is in said reaction zone;
    (d) discharging said medium from said outlet into a separation zone at a position above said inlet;
    (e) separating a gas phase from a liquid phase of said medium when the medium is in said separation zone, the medium flowing in a direction through the separation zone from the outlet of the reaction zone to the inlet of the reaction zone;
    (f) collecting the thus separated liquid phase in a lower portion of the separation zone;
    (g) collecting the thus separated gas phase in an upper portion of said separation zone and removing at least a portion of the thus collected gas phase; and
    (h) removing product, produced by fermentation and contained in the medium, from said separation zone, said tubular member having a volume greater than that of the separation zone.

2. The method as set forth in claim 1 including:
    (a) removing heat from said medium as the medium flows through said reaction zone.

3. The method as set forth in claim 2 wherein:
    (a) a portion of said medium is removed from said separation zone and conducted to a second separation zone where the thus removed medium containing product is separated into a gas phase and a liquid phase by foam breaker.

4. The method as set forth in claim 2 including:
    (a) flowing said medium over at least one generally horizontally disposed tray in said separation zone and allowing at least a portion of the gas phase to escape from said medium.

5. The method as set forth in claim 2 including:
    (a) mixing said medium by flowing same past mixing devices as same flows through said reaction zone; and wherein
    (b) said oxygen is introduced into said medium at a plurality of positions between the inlet and outlet of said reaction zone.

6. The method as set forth in claim 2 including:
    (a) increasing the surface area of said medium in said separation zone for release of a gas component of the medium from the medium.

7. The method as set forth in claim 2 including:
    (a) mixing the medium as the medium flows along the flow path.

8. The method as set forth in claim 7 wherein:
    (a) said oxygen containing gas is introduced into the medium at a plurality of points along the length of the reactor zone.

* * * * *